US00PP32615P2

(12) United States Plant Patent
Danziger

(10) Patent No.: US PP32,615 P2
(45) Date of Patent: Dec. 8, 2020

(54) ***JAMESBRITTENIA* PLANT NAMED 'DJAMGOL'**

(50) Latin Name: ***Jamesbrittenia breviflora* x *grandiflora***
Varietal Denomination: DJAMGOL

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 16/602,749

(22) Filed: Dec. 3, 2019

(51) Int. Cl.
*A01H 5/02* (2018.01)
*A01H 6/00* (2018.01)

(52) U.S. Cl.
USPC ..... Plt./485

(58) Field of Classification Search
USPC ..... Plt./263.1, 485
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct cultivar of *Jamesbrittenia* plant named 'DJAMGOL' is disclosed, characterized by stable, bright yellow flowers, and semi-erect habit. Plants are less sensitive to foliar disease. The new variety is a *Jamesbrittenia*, normally produced as an outdoor garden or container plant.

2 Drawing Sheets

Figure 1:
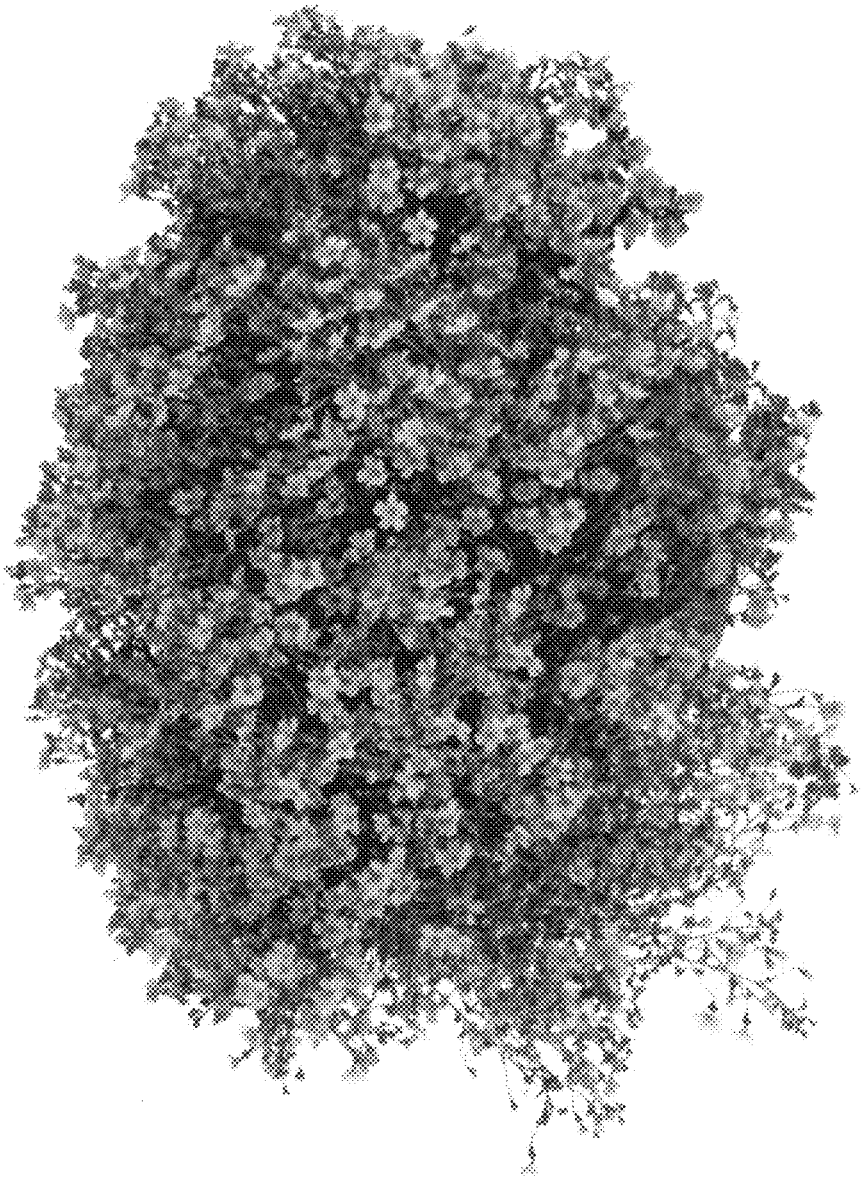

Latin name of the genus and species: *Jamesbrittenia breviflora* x *grandiflora*.

Variety denomination: 'DJAMGOL'.

BACKGROUND OF THE INVENTION

The new *Jamesbrittenia* cultivar is a product of a planned breeding program conducted by the inventor, Gavriel Danziger, in Moshav Mishmar Hashiva, Israel. The objective of the breeding program was to produce new *Jamesbrittenia* varieties for ornamental commercial applications. The crossing resulting in this new variety was made during Spring of 2014.

The seed parent is the unpatented, unnamed proprietary *Jamesbrittenia*. The pollen parent is different unpatented *Jamesbrittenia* 'ST-11-2359'. The pollen parent is the unpatented *Jamesbrittenia* 'ST-12-2364'. The new variety was discovered in Spring of 2015 by the inventor in a group of seedlings resulting from the 2014 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in Spring of 2015 and has shown that the unique features of this cultivar are stable and reproduced true to type in more than 20 successive generations.

SUMMARY OF THE INVENTION

The cultivar 'DJAMGOL' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DJAMGOL' These characteristics in combination distinguish 'DJAMGOL' as a new and distinct *Jamesbrittenia* cultivar:

1 Bright yellow flower color.
2. More stable flower color.
3. Less sensitivity to foliar disease (*Botrytis*).

Plants of the new cultivar 'DJAMGOL' are similar to plants of the seed parent in most horticultural characteristics, however, plants of the new cultivar 'DJAMGOL' differ in the following;

1. The new variety has yellow flowers, while the seed parent has magenta flowers.
2. The new variety has more stable flower color than the seed parent.

Plants of the new cultivar 'DJAMGOL' are similar to plants of the pollen parent in most horticultural characteristics, however, plants of the new cultivar 'DJAMGOL' differ in the following;

1. The new variety has a brighter flower color than the pollen parent.
2. The new variety has more stable flower color than the pollen parent.
3. The new variety is less sensitive to foliar disease than the pollen parent.

COMMERCIAL COMPARISON

Plants of the new cultivar 'DJAMGOL' are comparable to the patented commercial variety *Jamesbrittenia breviflora* 'Summer Dream Light Yellow', unpatented. The varieties are similar in most horticultural characteristics; however, the new variety 'DJAMGOL' differs in the following:

1. The new variety has brighter flowers than this comparator.
2. The new variety has larger flowers than this comparator.
3. The new variety has heavier foliage than this comparator.

BRIEF DESCRIPTION OF THE PHOTOGRAPHS

The accompanying photograph in FIG. 1 illustrates in full color a typical plant of 'DJAMGOL' grown in a greenhouse, in a 20 cm pot. Age of the plant photographed is approximately 2 months old from a rooted cutting.

Figure 2:
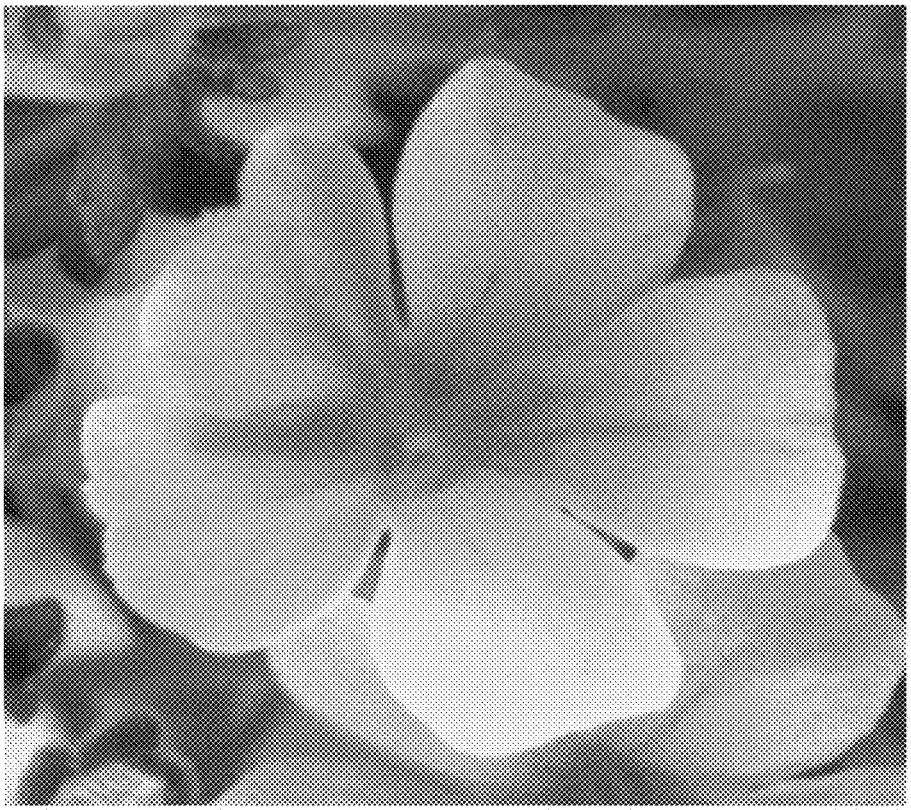

FIG. 2 illustrates a close up of a typical flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DJAMGOL' plants grown February to July in moderate climate in a greenhouse, in Moshav Mishmar Hashiva, Israel. The growing temperature ranged from 20° C. to 30° C. during the day and from 12° C. to 16° C. during the night. General light conditions are normal sunlight and numerical values represent averages of typical plant types. Botanical classification: *Jamesbrittenia breviflora* x *grandiflora* 'DJAMGOL'.

PROPAGATION

Time to initiate roots: 16-18 days at 22-26° C.
Root description: Roots quickly with a fine but robust root system.

PLANT

Age of plant described: Approximately 60 days from rooted cutting.
Container size of the plant described: 20 cm.
Growth habit: Semi-erect.
Height: 40 cm.
Plant spread: 60 cm.
Growth rate: Early.
Characteristics of primary lateral branches:
- *Quantity.*—6-7.
- *Form.*—Circular.
- *Diameter.*—0.38 cm.
- *Average length range.*—40-50 cm.
- *Color.*—RHS Yellow-Green 143D.
- *Texture.*—Smooth, slightly pubescent.
- *Strength.*—Brittle.

Internode length: 2.5 cm.

FOLIAGE

Leaf:
- *Arrangement.*—Alternate.
- *Quantity.*—Approximately 60 per branch.
- *Average length.*—1.5 cm.
- *Average width.*—1.25 cm.
- *Apex.*—Blunt.
- *Margin.*—Serrate.
- *Texture of top surface.*—Slightly pubescent.
- *Texture of bottom surface.*—Slightly pubescent.
- *Color.*—Young foliage upper side: RHS Yellow-Green 147B. Young foliage under side: RHS Yellow-Green 146B. Mature foliage upper side: RHS Yellow-Green 147B. Mature foliage under side: RHS Yellow-Green 146B.
- *Venation.*—Type: Pinnate. Venation color upper side: RHS Yellow-Green 147B. Venation color under side: RHS Yellow-Green 146B.
- *Petiole.*—Length: About 0.8 cm. Diameter: About 0.1 cm. Color: RHS Yellow-Green 146D.
- *Texture.*—Pubescent.

FLOWER

Natural flowering season: Spring.
Days to flowering from rooted cutting: 6-8 weeks.
Inflorescence and flower type and habit: Single, semi-trailing, upright.
Rate of flower opening: 2-3 days from bud to fully opened flower.
Flower longevity on plant: 6-7 days.
Persistent or self-cleaning: Self-cleaning.
Bud:
- *Length.*—About 1 cm.
- *Diameter.*—About 0.6 cm.
- *Color.*—RHS Yellow-Green 146C.

Flower size:
- *Diameter.*—About 2 cm.
- *Length.*—About 1.2 cm.
- *Corolla tube diameter.*—About 0.2 cm.

Corolla/petals:
- *Arrangement.*—Flat.
- *Lobe length.*—About 0.5 cm.
- *Lobe width.*—About 0.8 cm.
- *Quantity.*—5.
- *Texture.*—Smooth.
- *Lobe apex.*—Blunt.
- *Margin.*—Smooth.

Color:
- *When opening.*—Upper surface: RHS Yellow 15A. Lower surface: RHS Yellow 16D.
- *Fully opened.*—Upper surface: RHS Yellow 15B. Lower surface: RHS Yellow 16D.

Calyx/sepals:
- *Quantity per flower.*—5.
- *Length.*—About 0.5 cm.
- *Width.*—About 0.15 cm.
- *Apex.*—Blunt.
- *Base.*—Slightly tapered.
- *Margin.*—Smooth.
- *Texture.*—Pubescent.
- *Color.*—Upper Surface: RHS Yellow-Green 143A. Lower Surface: RHS Yellow-Green 143B.

Peduncle: None.
Pedicel:
- *Length.*—Approximately 1.7 cm.
- *Diameter.*—Approximately 0.1 cm.
- *Color.*—Near RHS Yellow-Green 144A.
- *Orientation.*—Alternate.
- *Pubescence.*—Pubescent.

Fragrance: None.

REPRODUCTIVE ORGANS

Stamens:
- *Number.*—5.
- *Filament length.*—Approximately 0.9 cm.

Anthers:
- *Shape.*—Oblong.
- *Length.*—Approximately 0.1 cm.
- *Color.*—RHS Yellow 13A.
- *Pollen.*—Color: RHS Yellow 13A. Quantity: Plentiful.

Pistil:
- *Number.*—1.
- *Length.*—About 0.9 cm.
- *Style.*—Not discernable.
- *Stigma.*—Not discernable.

OTHER CHARACTERISTICS

Seeds and fruits: Seeds very small, round and black in color.

Disease/pest resistance: Generally is not sensitive to pests but under high humidity *Botrytis* can occur.

Temperature tolerance: Good tolerance to high temperatures with only slight fading of the flower color.

What is claimed is:

1. A new and distinct cultivar of *Jamesbrittenia* plant named 'DJAMGOL' as herein illustrated and described.

* * * * *